(12) United States Patent
Ray et al.

(10) Patent No.: US 6,909,775 B2
(45) Date of Patent: Jun. 21, 2005

(54) COMPUTED TOMOGRAPHY GANTRY COOLING SYSTEMS AND METHODS

(75) Inventors: Shawn A. Ray, Menomonee Falls, WI (US); Charles B. Kendall, Brookfield, WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 233 days.

(21) Appl. No.: 10/319,947

(22) Filed: Dec. 16, 2002

(65) Prior Publication Data

US 2004/0114723 A1 Jun. 17, 2004

(51) Int. Cl.[7] .................................................. H01J 35/10
(52) U.S. Cl. ...................................... 378/141; 378/199
(58) Field of Search ................................ 378/141, 199, 378/200–202, 4–20

(56) References Cited

U.S. PATENT DOCUMENTS 4,969,167 A * 11/1990 Zupancic et al. ............. 378/19
5,761,269 A * 6/1998 Sugihara et al. ............ 378/199
5,982,843 A * 11/1999 Bailey et al. .................. 378/4
6,491,428 B1 * 12/2002 Takanashi .................... 378/200

FOREIGN PATENT DOCUMENTS

JP         61099134 A  *  5/1986  .................. 378/199
JP         07313500 A  * 12/1995  ............ A61B/6/03

* cited by examiner

Primary Examiner—Craig E. Church
Assistant Examiner—Krystyna Suchecki
(74) Attorney, Agent, or Firm—Christopher L. Bernard, Esq.

(57) ABSTRACT

A computed tomography ("CT") gantry cooling system including a gantry housing defining a gantry chamber, wherein the gantry housing includes a lower portion, an upper portion, and a gantry cover disposed adjacent to the upper portion of the gantry housing. The CT gantry cooling system also including a fan disposed within the gantry cover of the gantry housing, wherein the fan is operable for forcing cooling air into the gantry chamber and creating a positive pressure within the gantry chamber. The CT gantry cooling system further including a vent disposed within the gantry cover of the gantry housing, wherein the vent is operable for exhausting heated air from the gantry chamber.

25 Claims, 3 Drawing Sheets

COMPUTED TOMOGRAPHY GANTRY COOLING SYSTEMS AND METHODS

FIELD OF THE INVENTION

The present invention relates generally to computed tomography ("CT") systems and methods. More specifically, the present invention relates to CT gantry cooling systems and methods.

BACKGROUND OF THE INVENTION

Computed tomography ("CT") gantry electronic and mechanical systems, such as x-ray tubes, data acquisition system converter cards, power supplies, and the like, are relatively inefficient and generate a significant amount of heat during normal operation. Typically, this heat is trapped within a chamber, referred to herein as a gantry chamber, which is defined by a relatively large box-like structure or housing having a hole running through it. This housing is referred to as a gantry housing or, simply, a gantry. A moveable table engages the hole in the gantry and is operable for supporting and aligning a patient or the like in relation to the x-ray tube and the like. Other components disposed within the gantry chamber are relatively sensitive to temperature. For example, one or more detectors, which are operable for receiving x-rays that have been transmitted through the patient or the like and generating an image, consist of a material that is relatively sensitive to temperature. In conventional CT systems, the one or more detectors each incorporate a heater that is thermostatically controlled in order to maintain a relatively constant temperature. If the air disposed within the gantry chamber becomes too hot, the temperature of the one or more detectors may not be adequately controlled and overall CT system performance may suffer.

Typically, the gantry chamber is evacuated, allowing air to be drawn from the lower portion of the CT system, near the floor, and from the perimeter of the gantry chamber and expelled out of the upper portion of the gantry chamber, through the upper portion of the gantry housing, thereby cooling the gantry chamber. Alternatively, expensive air conditioning units and/or cooling software packages are used. Such conventional CT systems and methods do little to provide for mixing of the air disposed within the gantry chamber, resulting in inadequate cooling of the gantry and its components. Additionally, drawing air from the lower portion of the CT system, near the floor, and expelling it out of the upper portion of the gantry chamber, through the upper portion of the gantry housing, causes a significant amount of dust to accumulate within the gantry chamber and collect on the sensitive components disposed therein. Typically, this problem is remedied using special dust filters or via special room requirements.

Thus, what is needed are systems and methods that effectively cool the gantry chamber of a CT system, adequately mixing the air disposed within the gantry chamber, without the need for expensive air conditioning units and/or cooling software packages. What is also needed are CT gantry cooling systems and methods that prevent dust from accumulating within the gantry chamber and collecting on the sensitive components disposed therein, without the need for special dust filters or room requirements. What is further needed are CT gantry cooling systems and methods that minimize noise generation through optimized airflow requirements, enhancing patient and operator comfort.

BRIEF SUMMARY OF THE INVENTION

The computed tomography ("CT") gantry cooling systems and methods of the present invention use a plurality of fans and vents disposed within the gantry covers of a CT system's gantry housing. These fans and vents are specifically configured and provide for the effective cooling of the CT gantry electronic and mechanical systems by pressurizing the gantry chamber, rather than evacuating it. This pressurization allows high-speed cooling air to be effectively directed at the rotating and/or stationary components disposed within the gantry chamber. Advantageously, a heat exchanger disposed within the gantry chamber is positioned proximal to several of the vents and exhausts air along a path that bypasses many of the temperature-sensitive CT gantry electronic and mechanical systems. Increased cooling efficiency means that relatively quiet fans may be used, minimizing overall CT system noise generation. The position of the fans and the pressurization of the gantry chamber prevent dust from accumulating within the gantry chamber and collecting on the sensitive components disposed therein.

In one embodiment of the present invention, an x-ray generating system includes a housing defining a chamber, wherein the housing includes a lower portion, an upper portion, and a first cover disposed adjacent to the upper portion of the housing. The x-ray generating system also includes an x-ray generating device disposed within the chamber, wherein the x-ray generating device is operable for generating x-rays and residual heat. The x-ray generating system further includes a first fan disposed within the first cover of the housing, wherein the first fan is operable for forcing cooling air into the chamber and creating a positive pressure within the chamber. The x-ray generating system still further includes a first vent disposed within the first cover of the housing, wherein the first vent is operable for exhausting heated air from the chamber.

In another embodiment of the present invention, a computed tomography ("CT") system includes a gantry housing defining a gantry chamber, wherein the gantry housing includes a lower portion, an upper portion, and a first gantry cover disposed adjacent to the upper portion of the gantry housing. The CT system also includes an x-ray tube disposed within the gantry chamber, wherein the x-ray tube is operable for generating x-rays and residual heat. The CT system further includes a first fan disposed within the first gantry cover of the gantry housing, wherein the first fan is operable for forcing cooling air into the gantry chamber and creating a positive pressure within the gantry chamber. The CT system still further includes a first vent disposed within the first gantry cover of the gantry housing, wherein the first vent is operable for exhausting heated air from the gantry chamber.

In a further embodiment of the present invention, a computed tomography ("CT") gantry cooling system includes a gantry housing defining a gantry chamber, wherein the gantry housing includes a lower portion, an upper portion, and a gantry cover disposed adjacent to the upper portion of the gantry housing. The CT gantry cooling system also includes a fan disposed within the gantry cover of the gantry housing, wherein the fan is operable for forcing cooling air into the gantry chamber and creating a positive pressure within the gantry chamber. The CT gantry cooling system further includes a vent disposed within the gantry cover of the gantry housing, wherein the vent is operable for exhausting heated air from the gantry chamber.

In a still further embodiment of the present invention, a computed tomography ("CT") gantry cooling method includes providing a gantry housing defining a gantry chamber, wherein the gantry housing includes a lower portion, an upper portion, and a gantry cover disposed adjacent to the upper portion of the gantry housing. The CT gantry cooling method also includes providing a fan disposed within the gantry cover of the gantry housing. The CT gantry cooling method further includes forcing cooling air into the gantry chamber using the fan and creating a positive pressure within the gantry chamber using the fan. The CT gantry cooling method still further includes providing a vent disposed within the gantry cover of the gantry housing and exhausting heated air from the gantry chamber using the vent.

DETAILED DESCRIPTION OF THE INVENTION

As described above, the computed tomography ("CT") gantry cooling systems and methods of the present invention use a plurality of fans and vents disposed within the gantry covers of a CT system's gantry housing. These fans and vents are specifically configured and provide for the effective cooling of the CT gantry electronic and mechanical systems by pressurizing the gantry chamber, rather than evacuating it. This pressurization allows high-speed cooling air to be effectively directed at the rotating and/or stationary components disposed within the gantry chamber. Advantageously, a heat exchanger disposed within the gantry chamber is positioned proximal to several of the vents and exhausts air along a path that bypasses many of the temperature-sensitive CT gantry electronic and mechanical systems. Increased cooling efficiency means that relatively quiet fans may be used, minimizing overall CT system noise generation. The position of the fans and the pressurization of the gantry chamber prevent dust from accumulating within the gantry chamber and collecting on the sensitive components disposed therein.

Figure 1:
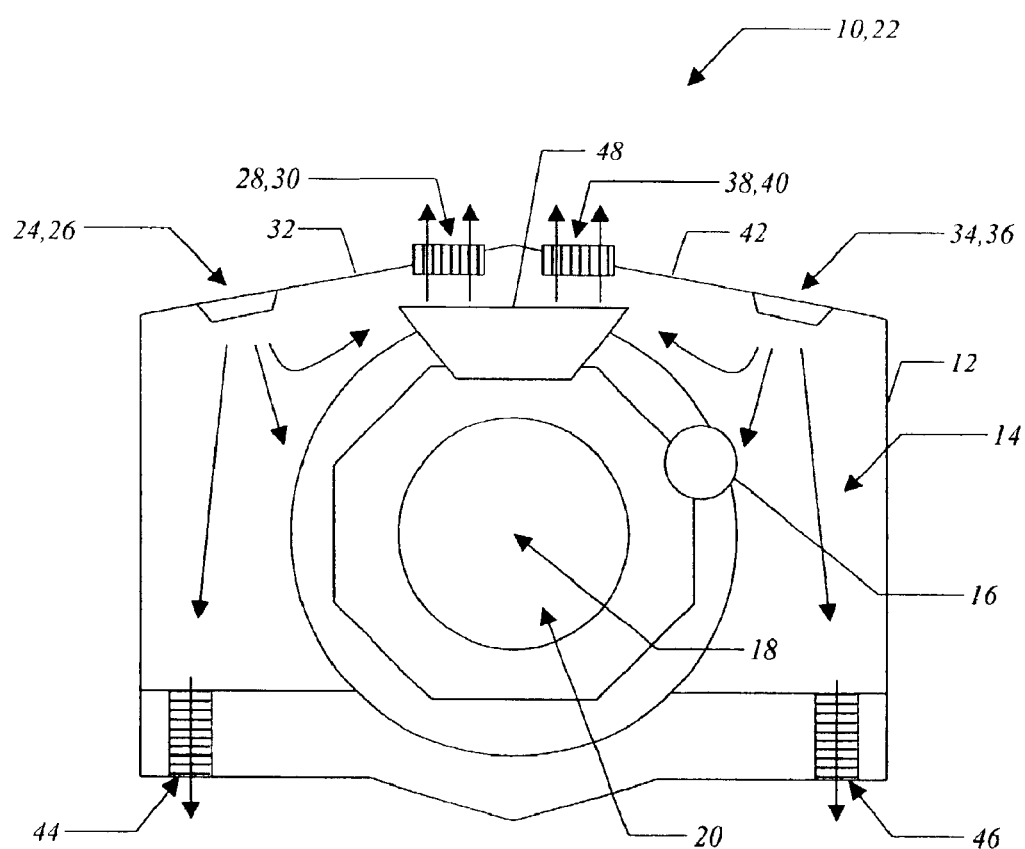
FIG. 1 is a schematic diagram illustrating one preferred embodiment of a computed tomography ("CT") gantry cooling system of the present invention, highlighting the placement of a plurality of fans and vents within the gantry covers of a CT system's gantry housing.

Referring to FIG. 1, in one embodiment of the present invention, a CT system 10 includes a gantry 12, also referred to herein as a gantry housing 12, forming and encompassing a gantry chamber 14. An x-ray tube 16 operable for generating x-rays and transmitting them through a patient or the like, one or more detectors (not shown) operable for receiving the x-rays that have been transmitted through the patient or the like and generating an image, and other electronic and mechanical systems are disposed within the gantry chamber 14. Preferably, the components disposed within the gantry chamber 14 rotate about an axis 18 that is coincident with the centerline of a hole 20 defined by the interior portion of the gantry housing 12. A moveable table (not shown) engages the hole 20 and is operable for supporting and aligning the patient or the like in relation to the x-ray tube 16, the one or more detectors, and the like. Many of the components disposed within the gantry chamber 14 are relatively sensitive to temperature. For example, the one or more detectors consist of a material that is relatively sensitive to temperature, and must remain below about 38 degrees C. In conventional CT systems, the one or more detectors each incorporate a heater that is thermostatically controlled in order to maintain a relatively constant temperature. If the air disposed within the gantry chamber 14 becomes too hot, the temperature of the one or more detectors may not be adequately controlled and overall CT system performance may suffer. Thus, the ambient temperature within the gantry chamber 14 is maintained at or below about 37 degrees C. using the gantry cooling systems and methods of the present invention.

In one exemplary embodiment, the x-ray tube 16 includes opposed electrodes enclosed within a cylindrical vacuum vessel. The vacuum vessel is typically fabricated from a glass or a metal, such as stainless steel, copper, or a copper alloy. The electrodes include a cathode assembly positioned at some distance from the target track of a rotating, disc-shaped anode assembly. Alternatively, such as in industrial applications, the anode assembly may be stationary. The target track, or impact zone, of the anode is generally fabricated from a refractory metal with a high atomic number, such as tungsten or a tungsten alloy. Further, to accelerate electrons used to generate x-rays, a voltage difference of about 60 kV to about 140 kV is typically maintained between the cathode and anode assemblies. The hot cathode filament emits thermal electrons that are accelerated across the potential difference, impacting the target zone of the anode assembly at high velocity. A small fraction of the kinetic energy of the electrons is converted to high-energy electromagnetic radiation, or x-rays, while the balance is contained in back-scattered electrons or converted to heat. The x-rays are emitted in all directions, emanating from a focal spot, and may be directed out of the vacuum vessel along a focal alignment path. In an x-ray tube 16 having a metal vacuum vessel, for example, an x-ray transmissive window is fabricated into the vacuum vessel to allow an x-ray beam to exit at a desired location. After exiting the vacuum vessel, the x-rays are directed along the focal alignment path to penetrate an object, such as a human anatomical part for medical examination and diagnostic purposes. The x-rays transmitted through the object are intercepted by the one or more detectors and an image of the internal anatomy of the object is formed. Likewise, industrial x-ray tubes may be used, for example, to inspect metal parts for cracks or to inspect the contents of luggage at an airport.

Since the production of x-rays in a medical diagnostic x-ray tube 16 is by its nature a very inefficient process, the components in the x-ray tube 16 operate at elevated temperatures. For example, the temperature of the anode's focal spot may run as high as about 2,700 degrees C., while the temperature in other parts of the anode may run as high as about 1,800 degrees C. The thermal energy generated during x-ray tube operation is typically transferred from the anode and other components to the vacuum vessel and into the gantry chamber 14.

Figure 2:
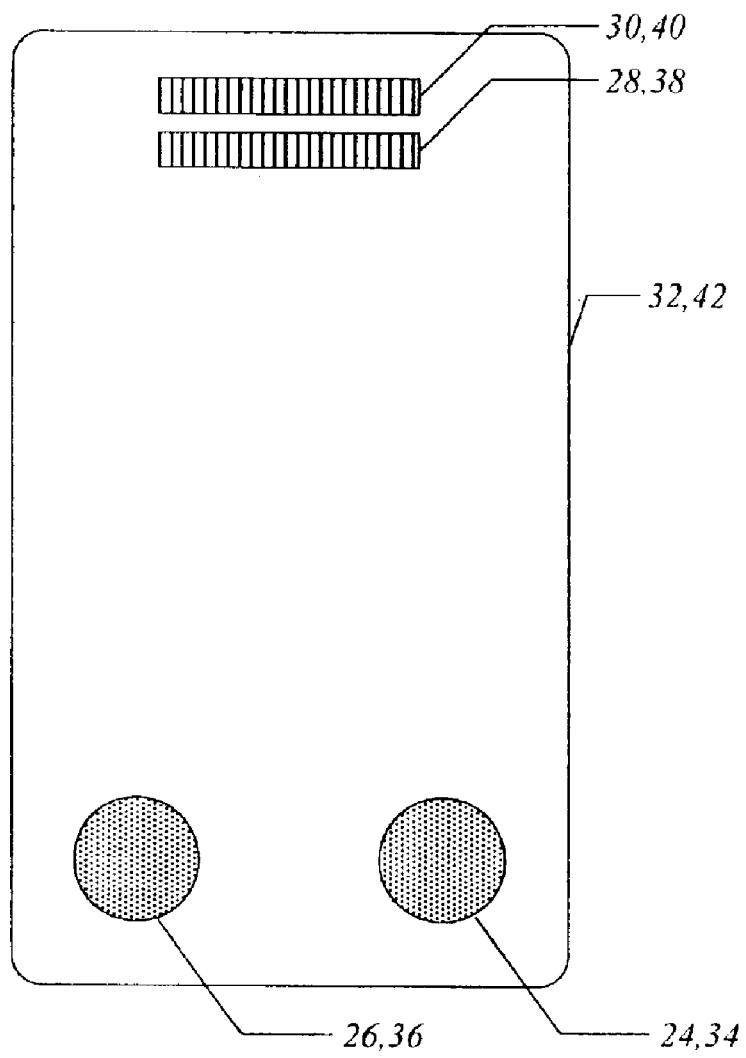
FIG. 2 is a top view of one preferred embodiment of one of the gantry covers of FIG. 1, again highlighting the placement of a plurality of fans and vents within the gantry cover.

The CT gantry cooling system 22 of the present invention includes a plurality of fans and vents that are specifically configured to cool the gantry 12 of the CT system 10. In one exemplary configuration, a pair of fans (including a first fan 24 and a second fan 26) and a pair of vents (including a first vent 28 and an optional second vent 30) are disposed within the first gantry cover 32 of the gantry housing 12. Another pair of fans (including a third fan 34 and a fourth fan 36) and another pair of vents (including a third vent 38 and an optional fourth vent 40) are disposed within the second gantry cover 42 of the gantry housing 12. Referring to FIG. 2, the first fan 24, the second fan 26, the first vent 28, the optional second vent 30, the third fan 34, the fourth fan 36, the third vent 38, and the optional fourth vent 40 are illustrated and are disposed within the first/second gantry cover 32,42. It will be readily apparent to those of ordinary skill in the art that, although a first fan 24, a second fan 26, a first vent 28, an optional second vent 30, a third fan 34, a fourth fan 36, a third vent 38, and an optional fourth vent 40 have been illustrated and described herein, a greater or lesser number of fans and vents may be used.

Referring again to FIG. 1, the plurality of fans and vents, described above, serve to pressurize the gantry chamber 14 of the CT system 10. Specifically, the plurality of fans and vents generate a cooling airflow that is directed at and around the components disposed within the gantry chamber 14, thereby cooling the components disposed within the gantry chamber 14. A first exhaust vent 44 and a second exhaust vent 46 are provided at the lower portion of the gantry housing 12 and the CT system 10, near the floor. Exhaust air from the lower portion of the CT system 10, near the floor, prevents dust from accumulating within the gantry chamber 14 and collecting on the sensitive components disposed therein.

Advantageously, the plurality of fans and vents, described above, also serve to mix the air disposed within the gantry chamber 14 of the CT system 10. The CT gantry cooling system 22 of the present invention performs a majority of its cooling functions while the components disposed within the gantry chamber 14 are in a stationary, non-rotating, position, such as when the CT system 10 is in a non-scanning operation mode. In a preferred configuration, the x-ray tube 16 is positioned within the upper portion of the gantry 12, proximal to the vents 28,30,38,40 disposed therein, during such a non-scanning operation mode, providing maximum cooling of the x-ray tube 16. Such a configuration prevents the x-ray tube 16 from ingesting its own heated air. Optionally, a heat exchanger 48 is also positioned within the upper portion of the gantry 12, proximal to the vents 28,30,38,40 disposed therein. The heat exchanger 48 serves to draw additional heat away from the x-ray tube 16 during the non-scanning operation mode and directly exhaust it out through the vents disposed within the upper portion of the gantry housing 12, thus not introducing additional hot air into the gantry chamber 14.

Figure 3:
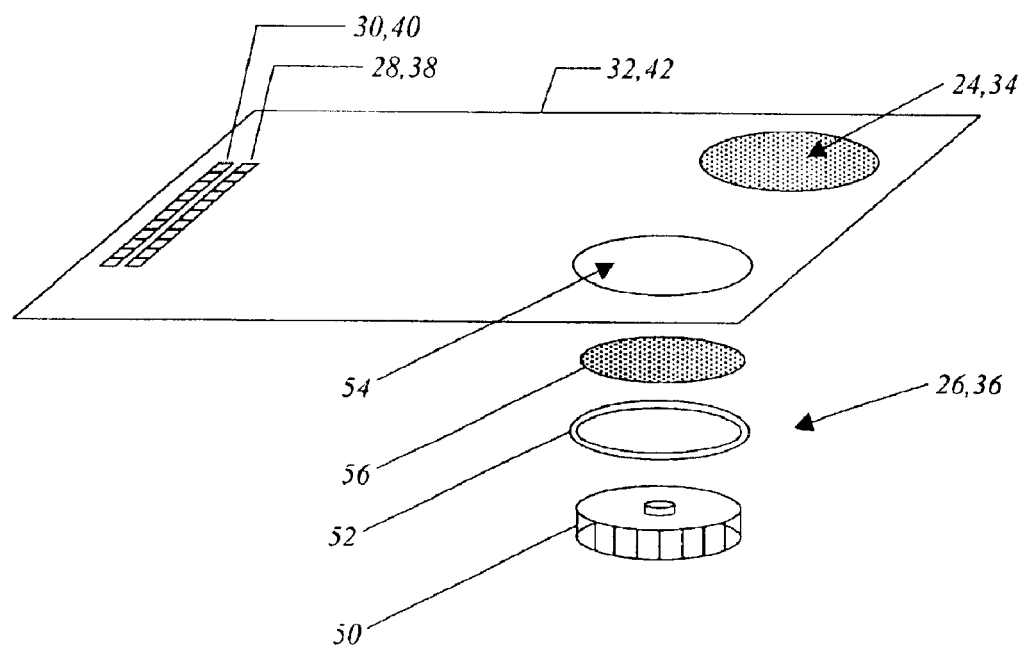
FIG. 3 is a partially-exploded perspective view of the gantry cover of FIG. 2, highlighting the components of one of the fan assemblies.

Referring to FIG. 3, in another embodiment of the present invention, each of the fans 24,34,26,36 disposed with each of the gantry covers 32,42 include a multi-speed fan assembly 50 coupled to a contoured intake 52 and disposed within an opening 54 in the respective gantry cover 32,42. Each of the openings 54 is covered by a finger guard mesh 56 or the like. The plurality of fans 24,34,26,36 may include, for example, a plurality of multi-speed AC fans, or a plurality of DC fans providing multiple operating points. Preferably, the plurality of fans 24,34,26,36 are controlled by a thermistor disposed within the gantry chamber 14 (FIG. 1) and are only used when the temperature within the gantry chamber 14 reaches a predetermined level.

It is apparent that there have been provided, in accordance with the systems and methods of the present invention, CT gantry cooling systems and methods. Although the systems and methods of the present invention have been described with reference to preferred embodiments and examples thereof, other embodiments and examples may perform similar functions and/or achieve similar results. All such equivalent embodiments and examples are within the spirit and scope of the present invention and are intended to be covered by the following claims.

What is claimed is:

1. An x-ray generating system, comprising:
   a housing defining a chamber, wherein the housing comprises a lower portion, an upper portion, and a first cover disposed adjacent to the upper portion of the housing;
   an x-ray generating device disposed within the chamber, wherein the x-ray generating device is operable for generating x-rays and residual heat;
   a first fan disposed within the first cover of the housing, wherein the first fan is operable for forcing cooling air into the chamber and creating a positive pressure within the chamber;
   a first vent disposed within the first cover of the housing, wherein the first vent is operable for exhausting heated air from the chamber; and
   a first exhaust vent disposed within the lower portion of the housing, wherein the first exhaust vent is operable for exhausting heated air from the chamber.

2. The x-ray generating system of claim 1, further comprising a second fan disposed within the first cover of the housing, wherein the second fan is operable for forcing cooling air into the chamber and creating a positive pressure within the chamber.

3. The x-ray generating system of claim 1, further comprising a second vent disposed within the first cover of the housing, wherein the second vent is operable for exhausting heated air from the chamber.

4. The x-ray generating system of claim 1, further comprising a second cover disposed adjacent to the upper portion of the housing.

5. The x-ray generating system of claim 4, further comprising a third fan disposed within the second cover of the housing, wherein the third fan is operable for forcing cooling air into the chamber and creating a positive pressure within the chamber.

6. The x-ray generating system of claim 5, further comprising a fourth fan disposed within the second cover of the housing, wherein the fourth fan is operable for forcing cooling air into the chamber and creating a positive pressure within the chamber.

7. The x-ray generating system of claim 4, further comprising a third vent disposed within the second cover of the housing, wherein the third vent is operable for exhausting heated air from the chamber.

8. The x-ray generating system of claim 7, further comprising a fourth vent disposed within the second cover of the housing, wherein the fourth vent is operable for exhausting heated air from the chamber.

9. The x-ray generating system of claim 1, further comprising a second exhaust vent disposed within the lower portion of the housing, wherein the second exhaust vent is operable for exhausting heated air from the chamber.

10. The x-ray generating system of claim 1, further comprising a heat exchanger disposed adjacent to the x-ray generating device and the first vent, wherein the heat exchanger is operable for drawing heat from the x-ray generating device and exhausting heated air from the chamber through the first vent.

11. A computed tomography ("CT") system, comprising:
    a gantry housing defining a gantry chamber, wherein the gantry housing comprises a lower portion, an upper portion, and a first gantry cover disposed adjacent to the upper portion of the gantry housing;
    an x-ray tube disposed within the gantry chamber, wherein the x-ray tube is operable for generating x-rays and residual heat;

a first fan disposed within the first gantry cover of the gantry housing, wherein the first fan is operable for forcing cooling air into the gantry chamber and creating a positive pressure within the gantry chamber;

a first vent disposed within the first gantry cover of the gantry housing, wherein the first vent is operable for exhausting heated air from the gantry chamber; and a first exhaust vent disposed within the lower portion of the gantry housing, wherein the first exhaust vent is operable for exhausting heated air from the gantry chamber.

12. The CT system of claim 11, further comprising a second fan disposed within the first gantry cover of the gantry housing, wherein the second fan is operable for forcing cooling air into the gantry chamber and creating a positive pressure within the gantry chamber.

13. The CT system of claim 11, further comprising a second vent disposed within the first gantry cover of the gantry housing, wherein the second vent is operable for exhausting heated air from the gantry chamber.

14. The CT system of claim 11, further comprising a second gantry cover disposed adjacent to the upper portion of the gantry housing.

15. The CT system of claim 14, further comprising a third fan disposed within the second gantry cover of the gantry housing, wherein the third fan is operable for forcing cooling air into the gantry chamber and creating a positive pressure within the gantry chamber.

16. The CT system of claim 15, further comprising a fourth fan disposed within the second gantry cover of the gantry housing, wherein the fourth fan is operable for forcing cooling air into the gantry chamber and creating a positive pressure within the gantry chamber.

17. The CT system of claim 14, further comprising a third vent disposed within the second gantry cover of the gantry housing, wherein the third vent is operable for exhausting heated air from the gantry chamber.

18. The CT system of claim 17, further comprising a fourth vent disposed within the second gantry cover of the gantry housing, wherein the fourth vent is operable for exhausting heated air from the gantry chamber.

19. The CT system of claim 11, further comprising a second exhaust vent disposed within the lower portion of the gantry housing, wherein the second exhaust vent is operable for exhausting heated air from the gantry chamber.

20. The CT system of claim 11, further comprising a heat exchanger disposed adjacent to the x-ray tube and the first vent, wherein the heat exchanger is operable for drawing heat from the x-ray tube and exhausting heated air from the gantry chamber through the first vent.

21. A computed tomography ("CT") gantry cooling system, comprising:

a gantry housing defining a gantry chamber and having an x-ray tube disposed within the chamber, wherein the gantry housing comprises a lower portion, an upper portion, and a gantry cover disposed adjacent to the upper portion of the gantry housing;

a fan disposed within the gantry cover of the gantry housing, wherein the fan is operable for forcing cooling air into the gantry chamber and creating a positive pressure within the gantry chamber;

a vent disposed within the gantry cover of the gantry housing, wherein the vent is operable for exhausting heated air from the gantry chamber; and an exhaust vent disposed within the lower portion of the gantry housing, wherein the exhaust vent is operable for exhausting heated air from the gantry chamber.

22. The CT gantry cooling system of claim 21, further comprising a heat exchanger disposed adjacent to both the x-ray tube disposed within the gantry chamber and the vent, wherein the heat exchanger is operable for drawing heat from the x-ray tube and exhausting heated air from the gantry chamber through the vent.

23. A computed tomography ("CT") gantry cooling method, comprising:

providing a gantry housing defining a gantry chamber, wherein the gantry housing comprises a lower portion, an upper portion, and a gantry cover disposed adjacent to the upper portion of the gantry housing; providing an x-ray tube within the gantry chamber;

providing a fan disposed within the gantry cover of the gantry housing;

forcing cooling air into the gantry chamber using the fan;

creating a positive pressure within the gantry chamber using the fan;

providing a vent disposed within the gantry cover of the gantry housing;

exhausting heated air from the gantry chamber using the vent;

providing an exhaust vent disposed within the lower portion of the gantry housing; and exhausting heated air from the gantry chamber using the exhaust vent.

24. The CT gantry cooling method of claim 23, further comprising providing a heat exchanger disposed adjacent to both the x-ray tube disposed within the gantry chamber and the vent.

25. The CT gantry cooling method of claim 24, further comprising drawing heat from the x-ray tube and exhausting heated air from the gantry chamber through the vent using the heat exchanger.

* * * * *